US008767914B2

(12) United States Patent
Teshima et al.

(10) Patent No.: US 8,767,914 B2
(45) Date of Patent: Jul. 1, 2014

(54) STRUCTURE, METHOD OF MANUFACTURING THE SAME, AND IMAGING APPARATUS

(75) Inventors: Takayuki Teshima, Yokohama (JP); Yutaka Setomoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 314 days.

(21) Appl. No.: 13/372,105

(22) Filed: Feb. 13, 2012

(65) Prior Publication Data

US 2012/0207275 A1 Aug. 16, 2012

(30) Foreign Application Priority Data

Feb. 15, 2011 (JP) ................................ 2011-030010

(51) Int. Cl.
*A61B 6/00* (2006.01)

(52) U.S. Cl.
USPC ................................ 378/62; 378/82; 378/145

(58) Field of Classification Search
USPC ............ 378/36, 62, 82, 145; 205/131; 216/37
See application file for complete search history.

(56) References Cited

U.S. PATENT DOCUMENTS

2011/0168908 A1* 7/2011 Wang et al. .............. 250/370.09
2012/0152895 A1* 6/2012 Chebi et al. ..................... 216/37
2013/0051530 A1* 2/2013 Nepomnishy et al. .......... 378/85
2013/0279651 A1* 10/2013 Yokoyama ...................... 378/36
2013/0343524 A1* 12/2013 Teshima .......................... 378/71

FOREIGN PATENT DOCUMENTS

JP 2010-185728 A 8/2010

* cited by examiner

*Primary Examiner* — Glen Kao
(74) *Attorney, Agent, or Firm* — Canon U.S.A., Inc., IP Division

(57) ABSTRACT

A method of manufacturing a structure includes a step of preparing a substrate including a silicon section, recessed sections and protruding sections formed by etching the silicon section, and a first insulating layer disposed on top portions of the protruding sections; a step of forming second insulating layers on sidewalls and bottom portions of the recessed sections; a step of forming seed layers containing metal above the bottom portions of the recessed sections; and a step of forming plating layers in such a manner that the recessed sections are filled with metal by electroplating. The second insulating layers contain an organopolysiloxane having at least one of a partial structure represented by the following formula (1) and a partial structure represented by the following formula (2):

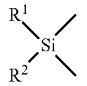

(1)

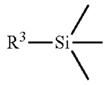

(2)

where $R^1$, $R^2$, and $R^3$ represent alkyl groups identical to or different from each other.

8 Claims, 4 Drawing Sheets

STRUCTURE, METHOD OF MANUFACTURING THE SAME, AND IMAGING APPARATUS

BACKGROUND OF THE INVENTION

1. Field of the Invention

The present invention relates to a structure, a method of manufacturing the structure, an imaging apparatus including the structure.

2. Description of the Related Art

Diffraction gratings having a periodic structure are used in various apparatuses as dispersive elements. In recent years, structures having a periodic structure made of a metal having high X-ray absorption are used in industrial applications such as nondestructive testing, medical applications such as roentgenography, and the like. Nondestructive testing and roentgenography exploit differences in X-ray absorption between elements contained in objects or living organisms or between differences in density therebetween to produce contrast images and are referred to as an X-ray absorption contrast method.

However, since light elements have extremely low X-ray absorption, it is difficult to image soft biological tissues or soft materials containing carbon, hydrogen, oxygen, and the like.

On the other hand, phase contrast methods using the phase difference between X-rays have been studied mainly in radiation facilities since the 1990s. Furthermore, phase imaging has been studied on a laboratory scale using X-ray tubes, thereby enabling a propagation method, a Talbot interference method, and the like in principle. In order to produce Talbot interference, a shield grating having a configuration in which X-ray permeable sections and X-ray shielding sections are periodically arranged is used. In the shield grating, the X-ray shielding sections include structures which are made of a metal, such as gold, having high X-ray absorption and which have a high aspect ratio (the aspect ratio is defined as the ratio (h/w) of the height or depth h to width w of each structure). A preferred method of manufacturing the shield grating is as follows: a mold is filled with a metal having high X-ray absorption by plating.

Japanese Patent Laid-Open No. 2010-185728 discloses a method in which a recessed section is formed in a silicon substrate by reactive ion etching and gold is precipitated in the recessed section by plating. In this method, a silicon oxide layer (electrically insulating layer) is formed over the bottom and wall of the recessed section by introducing an oxygen gas into an inductively coupled plasma treatment system and a portion of the silicon oxide layer that is located on the bottom is etched off, whereby a portion of the silicon substrate is exposed. The exposed portion is used as a seed layer during electroplating and gold is precipitated on the exposed portion.

However, a silicon oxide layer formed by introducing an oxygen gas into an inductively coupled plasma treatment system usually has a thickness of about 2 nm. Therefore, it is not necessarily easy for the silicon oxide layer, which serves as an insulating layer for electroplating, to keep sufficient insulation. In particular, in the case of forming a structure with a high aspect ratio, if a silicon oxide layer formed on a side wall thereof cannot keep sufficient insulation, voids (gaps) may possibly be formed because plating is precipitated on the side wall.

SUMMARY OF THE INVENTION

Aspects of the present invention provide a method of manufacturing a structure with a high aspect ratio, the method being capable of suppressing the formation of voids when a recessed section formed in silicon is filled with metal by plating.

A method of manufacturing a structure includes a step of preparing a substrate including a silicon section, recessed sections formed by etching the silicon section, protruding sections formed by etching the silicon section, and a first insulating layer disposed on top portions of the protruding sections; a step of forming second insulating layers on sidewalls and bottom portions of the recessed sections; a step of forming seed layers containing metal above the bottom portions of the recessed sections having the second insulating layers thereon; and a step of forming plating layers in such a manner that the recessed sections having the seed layers are filled with metal by electroplating. The second insulating layers contain an organopolysiloxane having at least one of a partial structure represented by the following formula (1) and a partial structure represented by the following formula (2):

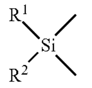
(1)

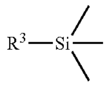
(2)

where $R^1$, $R^2$, and $R^3$ represent alkyl groups identical to or different from each other.

Other aspects of the present invention will be clarified in embodiments below.

Further features of the present invention will become apparent from the following description of exemplary embodiments with reference to the attached drawings.

DESCRIPTION OF THE EMBODIMENTS

The present invention relates to a method of manufacturing a structure. The method includes steps below.

(1) A first step of preparing a silicon substrate including a silicon section, recessed sections formed by etching the silicon section, protruding sections formed by etching the silicon section, and a first insulating layer disposed on top portions of the protruding sections.

(2) A second step of forming second insulating layers on sidewalls and bottom portions of the recessed sections, the second insulating layers containing an organopolysiloxane having at least one of a partial structure represented by the following formula (1) and a partial structure represented by the following formula (2):

(1)

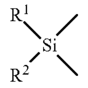

(2)

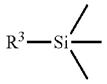

wherein $R^1$, $R^2$, and $R^3$ represent alkyl groups identical to or different from each other.

(3) A third step of forming seed layers containing metal above the bottom portions of the recessed sections having the second insulating layers thereon.

(4) A fourth step of forming plating layers in such a manner that the recessed sections having the seed layers are filled with metal by electroplating.

Embodiments of the present invention will now be described with reference to the attached drawings.

FIGS. 1A to 1D are illustrations showing steps of a method of manufacturing a structure according to an embodiment of the present invention.

(First Step)

Figure 1A:
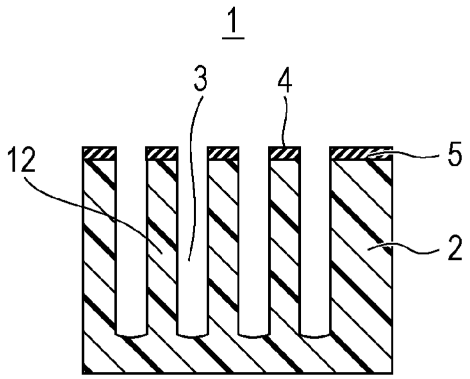
FIG. 1A is an illustration showing a first step of a method of manufacturing a structure according to an embodiment of the present invention.

A first step of preparing a silicon substrate 1 is first described. As shown in FIG. 1A, the silicon substrate 1 includes a silicon section 2, recessed sections 3 formed by etching the silicon section 2, protruding sections 12 formed by etching the silicon section 2, and a first insulating layer 5 disposed on top portions 4 of the protruding sections 12.

In this embodiment, the first step is performed in such a manner that the first insulating layer 5 is formed so as to have portions located on surface sites of the silicon section 2 that are to be the top portions 4 of the protruding sections 12 and the silicon section 2 is etched using the first insulating layer 5 as a mask.

The first insulating layer 5 may be made of an organic material, an inorganic material, or an organic-inorganic hybrid material. When the organic material is a photoresist, the first insulating layer 5 can be readily patterned by semiconductor photolithography. The inorganic material may be silicon oxide or silicon nitride. A layer of silicon oxide and a layer of silicon nitride can be patterned in such a manner that these layers are coated with a photoresist and are then treated by semiconductor photolithography and etching. The silicon oxide layer and the silicon nitride layer can be formed by chemical vapor deposition (CVD), vacuum sputtering, or vacuum vapor deposition. The silicon oxide layer can be formed by thermally oxidizing the surface of silicon.

The first insulating layer 5 is preferably made of $SiO_2$. A layer of $SiO_2$ sufficiently functions as an insulating layer used for electroplating. Such a layer can be formed by thermally oxidizing and patterning the surface of silicon as described above. The use of the silicon substrate 1, in which the first insulating layer 5 is disposed on the top portions 4 of the protruding sections 12, insulates the top portions 4, on which electric fields are likely to be concentrated during electroplating and therefore plating is likely to be precipitated, to suppress the precipitation of plating because the first insulating layer 5 is present on the top portions 4. When the first insulating layer 5 is not present, plating is precipitated on the top portions 4 and upper portions of the recessed sections 3 are blocked with plating layers 9; hence, voids may possibly be caused in portions of the plating layers 9 that are located in the recessed sections 3. In the case of using the plating layers 9 to absorb X-rays, such voids are the cause of absorption loss. When the first insulating layer 5 is made of $SiO_2$, the first insulating layer 5 preferably has a thickness of 5 nm or more.

Wet etching using an aqueous alkali solution can be used to etch the silicon section 2 by making use of the etching selectivity of the crystal orientation of the silicon section 2. Furthermore, ion sputtering and dry etching processes using reactive gas plasma or the like can also be used. Reactive ion etching (RIE) is among the dry etching processes using reactive gas plasma and is suitable for forming a structure with a high aspect ratio. In particular, the following process is suitable for forming a structure with a higher aspect ratio: a Bosch RIE process in which etching and the deposition of a sidewall-protecting layer are alternately performed using a $SF_6$ gas and a $C_4F_8$ gas, respectively.

After the recessed sections 3 and the protruding sections 12 are formed in the silicon section 2, the first insulating layer 5 may be formed on the top portions 4 of the protruding sections 12. In this case, the recessed sections 3 and the protruding sections 12 can be formed in the silicon section 2 by any one of the above etching processes. Furthermore, the first insulating layer 5 can be formed on the top portions 4 of the protruding sections 12 by vacuum sputtering or vacuum vapor deposition. A process of forming the first insulating layer 5 on the top portions 4 of the protruding sections 12 is not limited to vacuum sputtering or vacuum vapor deposition.

(Second Step)

Figure 1B:
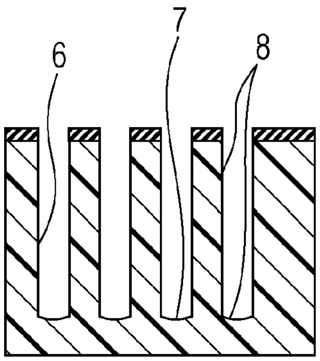
FIG. 1B is an illustration showing a second step of the structure-manufacturing method according to the embodiment.

A second step of forming second insulating layers 8 is described below. As shown in FIG. 1B, the second insulating layers 8 are formed on sidewalls 6 and bottom portions 7 of the recessed sections 3 formed in the silicon section 2. The second insulating layers 8 contain an organopolysiloxane having at least one of a partial structure represented by the following formula (1) and a partial structure represented by the following formula (2):

(1)

(2)

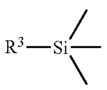

wherein $R^1$, $R^2$, and $R^3$ represent alkyl groups identical to or different from each other. An organopolysiloxane having the partial structure represented by Formula (1) is referred to as a dialkylpolysiloxane and an organopolysiloxane having the partial structure represented by Formula (2) is referred to as a monoalkylpolysiloxane in some cases.

In this embodiment, the second insulating layers 8 contain at least one of the dialkylpolysiloxane and the monoalkylpolysiloxane and are formed on the sidewalls 6 and bottom portions 7 of the recessed sections 3 formed in the silicon section 2. The second insulating layers 8, which are disposed on the sidewalls 6 and bottom portions 7 of the recessed sections 3 formed in the silicon section 2, function as insulating layers for suppressing the precipitation of plating layers on the sidewalls 6 during electroplating below. The precipitation of such plating layers on the sidewalls 6 promotes plating growth in portions of the sidewalls 6 that are located on the top portion 4 side from the bottom portions 7 and therefore can be the cause of forming voids.

In the case of forming the second insulating layers 8 using the dialkylpolysiloxane or the monoalkylpolysiloxane, the dialkylpolysiloxane or the monoalkylpolysiloxane forms repetitive structures represented by the following formula (3) or (4), respectively, on the sidewalls 6 and bottom portions 7 of the recessed sections 3 in the silicon section 2 to create the second insulating layers 8:

(3)

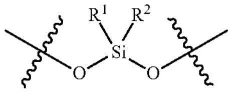

(4)

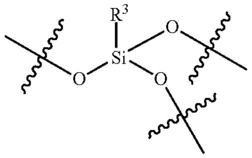

wherein $R^1$, $R^2$, and $R^3$ represent linear or branched alkyl groups identical to different from each other. The alkyl groups each represented by $R^1$, $R^2$, or $R^3$ preferably contain one to 12 carbon atoms and more preferably one to three carbon atoms.

When the second insulating layers 8 contain the dialkylpolysiloxane and the monoalkylpolysiloxane, the repetitive structures represented by Formula (3) and the repetitive structures represented by Formula (4) coexist.

The second insulating layers 8 are preferably formed by a vapor phase process. When the recessed sections 3 in the silicon section 2 have a high aspect ratio, forming the second insulating layers 8 by a liquid phase process causes sticking between the sidewalls 6 of the neighboring recessed sections 3 and therefore may possibly cause uneven pitches. In this embodiment, such a wet process is not used to form the second insulating layers 8 on the sidewalls 6 and bottom portions 7 of the recessed sections 3 in the silicon section 2; hence, the occurrence of sticking can be suppressed.

The term "high aspect ratio" as used herein means that the ratio (h/w) of the height h to width w of each recessed section 3 in the silicon section 2 is 5 or more and more preferably 12 to 60.

A procedure for forming the second insulating layers 8 by a vapor phase process is briefly described below. The second insulating layers 8 can be formed in such a manner that a precursor of the organopolysiloxane is vaporized and is subjected to hydrolysis and polycondensation in a vapor state. In particular, after the organopolysiloxane precursor is vaporized, the organopolysiloxane precursor may be hydrolyzed and polycondensated on the surfaces of the recessed sections 3 in the silicon section 2 in a vapor state. Natural oxide films are present on the sidewalls 6 and bottom portions 7 of the recessed sections 3 in the silicon section 2. After the vapor of the organopolysiloxane precursor enters the recessed sections 3 in the silicon section 2, the organopolysiloxane precursor is bonded to silanol groups (Si—OH) present on the surfaces of the natural oxide films through hydrolysis. Furthermore, the organopolysiloxane precursor bonded to the silanol groups on the surfaces of the natural oxide films and the vaporized organopolysiloxane precursor are polycondensated. This allows layers containing the repetitive structures represented by Formula (1) or (2) or layers containing the repetitive structures represented by Formula (1) and the repetitive structures represented by Formula (2) to be formed.

A layer containing a trialkylsilyl group represented by the formula $R_3Si$— is insufficient as an electrically insulating layer used for electroplating and therefore is preferably not used, wherein R represents an alkyl group. The trialkylsilyl group can only react with one silanol group. Therefore, after the trialkylsilyl group forms a bond with one of the silanol groups of the natural oxide films, the trialkylsilyl group cannot form another bond and is terminated. Thus, the trialkylsilyl group can only form an incomplete monolayer on a natural oxide film and therefore may possibly cause insufficient insulation.

On the other hand, a dialkylsilyl or monoalkylsilyl group can react with two or more silanol groups and therefore layers in which the partial structure represented by Formula (1) and the partial structure represented by Formula (2) are repeatedly arranged can be formed. The layers can maintain insulation.

The organopolysiloxane precursor may be a silane coupling agent. The use of the silane coupling agent in a vapor state allows the second insulating layers 8 to be formed of a dialkylpolysiloxane or a monoalkylpolysiloxane.

Examples of a silane coupling agent useful in producing the dialkylpolysiloxane include dimethyldimethoxysilane, dimethyldiethoxysilane, dimethyldichlorosilane, dimethyldibromosilane, diethyldimethoxysilane, diethyldiethoxysilane, diethyldichlorosilane, and dimethyldibromosilane.

Examples of a silane coupling agent useful in producing the monoalkylpolysiloxane include trimethoxymethylsilane, triethoxymethylsilane, trichloromethylsilane, tribromomethylsilane, trimethoxyethylsilane, triethoxyethylsilane, trichloroethylsilane, tribromoethylsilane, trimethoxypropylsilane, triethoxypropylsilane, trichloropropylsilane, tribromopropylsilane, trimethoxybutylsilane, triethoxybutylsilane, trichlorobutylsilane, tribromobutylsilane, decyltrichlorosilane, hexyltrimethoxysilane, cyclohexyltrichlorosilane, n-dodecyltriethoxysilane, n-octyltrichlorosilane, n-octyltriethoxysilane, octadecyltriethoxysilane, and pentyltriethoxysilane.

(Third Step)

Figure 1C:
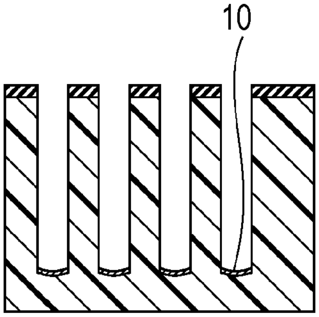
FIG. 1C is an illustration showing a third step of the structure-manufacturing method according to the embodiment.

A third step of forming seed layers 10 containing metal is described below. As shown in FIG. 1C, the seed layers 10 are formed above the bottom portions 7 of the recessed sections 3 having the second insulating layers 8.

In this embodiment, the seed layers 10 are formed on the second insulating layers 8.

A directional deposition process is used to form the seed layers 10. The directional deposition process is one capable of forming the seed layers 10 perpendicularly to the bottoms of the recessed sections 3 and is, for example, electron beam evaporation or resistive heating evaporation.

(Fourth Step)

Figure 1D:
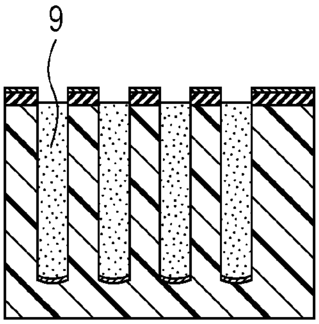
FIG. 1D is an illustration showing a fourth step of the structure-manufacturing method according to the embodiment.

A fourth step of forming the plating layers 9 is described below. As shown in FIG. 1D, the plating layers 9 are formed in such a manner that the recessed sections 3 having the seed layers 10 are filled with metal by electroplating.

The recessed sections 3 in the silicon section 2 are filled with metal by electroplating. In order to perform electroplating, electric power is applied to the seed layers 10 disposed on the bottom portions 7 of the recessed sections 3. Although some of the seed layers 10 are arranged on the first insulating layer 5 on the top portions 4, the seed layers 10 on the first insulating layer 5 are electrically insulated from the seed layers 10 on the bottom portions 7. Therefore, the plating layers 9 are not precipitated on the top portions 4.

The second insulating layers 8 are disposed on the side-walls 6 and the first insulating layer 5 is disposed on the top portions 4. Therefore, the plating layers 9 are selectively grown on the seed layers 10 on the bottom portions 7; hence, the formation of voids can be suppressed.

The metal filled in the recessed sections 3 is preferably gold or a gold alloy in view of high X-ray absorption and plating easiness. The use of a high X-ray absorption metal allows shielding sections to have a small thickness (height) and therefore allows the pitch between the shielding sections and permeable sections to be reduced. Therefore, an absorption grating, enabling imaging improved in spatial coherence, for radiation is obtained.

In general, it is not necessarily easy to directly generate plating nuclei uniformly in silicon; hence, a plating layer may possibly have an uneven thickness. The adhesion between silicon and gold is insufficient and therefore plating nuclei generated on silicon may possibly be lost. In this embodiment, the metal filled in the recessed sections 3 is grown on the seed layers 10 and therefore the possibility of such a plating problem can be reduced. After the metal is filled in the recessed sections 3 as described above, the silicon section 2 may be partly or entirely removed.

Features of this embodiment are described below.

The method of manufacturing the structure according to this embodiment can suppress the precipitation of plating on silicon sidewalls. Therefore, the formation of voids can be suppressed during the manufacture of a high-aspect ratio structure. Hence, a structure having a narrow pitch and a high aspect ratio can be manufactured.

Second insulating layers are formed in such a manner that a precursor of an organopolysiloxane is vaporized and is subjected to hydrolysis and polycondensation in a vapor state. Therefore, the sticking between neighboring silicon protruding sections can be avoided and insulating layers can be formed on silicon sidewalls.

Since the organopolysiloxane precursor is a silane coupling agent, the insulating layers can be formed on the silicon sidewalls without using any special apparatus.

A first insulating layer is made of $SiO_2$ and therefore the precipitation of plating on silicon top portions can be suppressed; hence, the formation of voids can be suppressed.

When metal filled by plating is gold or a gold alloy, the possibility of causing the unevenness of plating thickness and/or the loss of plating nuclei can be more reduced as compared to the case of filling gold or the gold alloy directly in the surface of silicon.

A structure obtained by the above method includes a silicon substrate including recessed sections and protruding sections and a first insulating layer disposed on top portions of the protruding sections. The structure further includes second insulating layers which are arranged on sidewalls and bottom portions of the recessed sections and which contain an organopolysiloxane having at least one of a partial structure represented by Formula (1) and a partial structure represented by Formula (2). The recessed sections having the second insulating layers are filled with metal.

The structure can be used as a shield grating for imaging apparatus performing a Talbot interference method. An imaging apparatus performing the Talbot interference method includes a diffraction grating diffracting an X-ray emitted from an X-ray source, a shield grating shielding a portion of the X-ray diffracted by the diffraction grating, and a detector for detecting the X-ray passing through the shield grating. The imaging apparatus can be used take an image of a sample placed between the X-ray source and diffraction grating or between the diffraction grating and the shield grating.

EXAMPLES

The present invention is further described below in detail with reference to examples.

Example 1

Figure 2A:
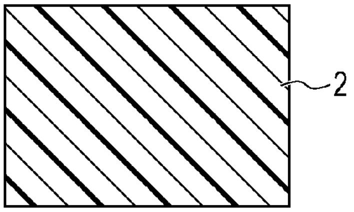
FIGS. 2A to 2G are illustrations showing a step of a method of manufacturing a structure according to Example 1 of the present invention.
Figure 2B:
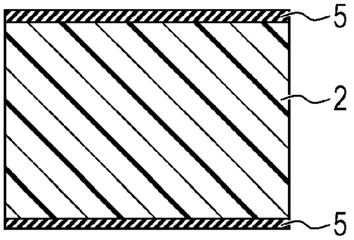

FIGS. 2A to 2G are illustrations showing steps of a method of manufacturing a structure according to Example 1 of the present invention. The method is described with reference to FIGS. 2A to 2G. In this example, the following wafer was used: a silicon wafer, equipped with two mirror-like surfaces, having a diameter of 100 mm (four inches) and a thickness of 525 μm as shown in FIG. 2A. $SiO_2$ was used to form a first insulating layer 5. $SiO_2$ layers with a thickness of about 1.0 μm were each formed on the front and back of the silicon wafer by thermally wet-oxidizing the silicon wafer at 1,050° C. for four hours as shown in FIG. 2B.

Figure 2C:
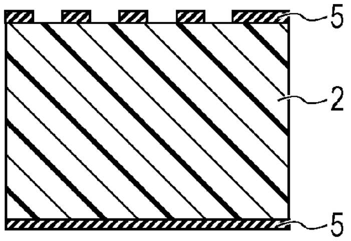

A Cr layer with a thickness of 200 nm was formed on one of the $SiO_2$ layers by an electron beam evaporation process. A positive resist was applied onto the Cr layer and was patterned by semiconductor photolithography, whereby a resist pattern having 2 μm ϕ sub-patterns two-dimensionally arranged at a pitch of 4 μm was formed. Exposed portions of the Cr layer were etched off using an aqueous Cr-etching solution, whereby the $SiO_2$ layer under the Cr layer was partly exposed. Exposed portions of this $SiO_2$ layer were etched off by a dry etching process using $CHF_3$ plasma, whereby the silicon wafer was partly exposed. The resist pattern was removed with dimethylformamide and the Cr layer was removed with the etching solution as shown in FIG. 2C.

Figure 2D:
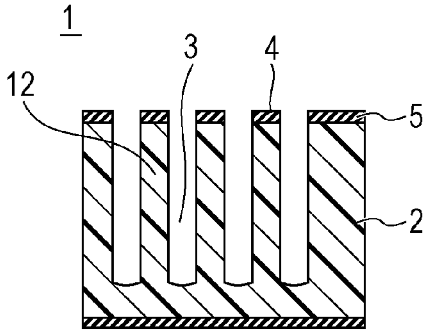

RIE was performed by a Bosch process in such a manner that this $SiO_2$ layer was used as a mask and etching and the deposition of a sidewall-protecting layer were alternately performed using a $SF_6$ gas and a $C_4F_8$ gas, respectively. As a result of RIE, recessed sections 3 with a depth of 65 μm and protruding sections 12 were formed as shown in FIG. 2D. This allowed a silicon structure including 2 μm ϕ silicon grids, arranged at a pitch of 4 μm, having a height of about 65 μm to be obtained. In this example, the silicon structure was used as a silicon substrate 1. The silicon substrate 1 included the first insulating layer 5 disposed on top portions 4 of the protruding sections 12 formed by etching a silicon section 2.

Figure 2E:
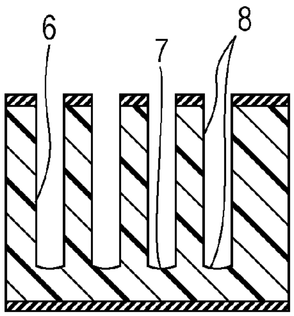

A petri dish containing trimethoxymethylsilane, a petri dish containing pure water, and the silicon substrate 1 were placed on a 100° C. hotplate and were covered with a petri dish lid. This allowed trimethoxymethylsilane to be vaporized. The vapor of trimethoxymethylsilane entered the recessed sections 3, resulting in the formation of second insulating layers 8 made of a monomethylpolysiloxane as shown in FIG. 2E. Since the silicon substrate 1 was heated on the hotplate, the trimethoxymethylsilane vapor was not condensed on the silicon substrate 1. After a lapse of four hours, the silicon substrate 1 was transferred onto a 150° C. hotplate and was then heated for 30 minutes.

Figure 2F:
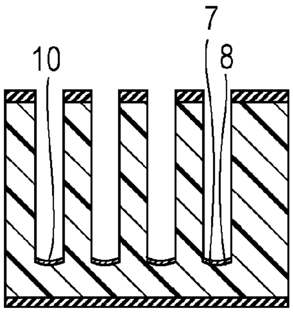

Chromium sub-layers and gold sub-layers for forming seed layers 10 were formed in that order using an electron beam evaporation system so as to have a thickness of about 7.5 nm and a thickness of about 50 nm, respectively. This allowed the seed layers 10 to be formed above bottom portions 7 of the recessed sections 3 in the silicon section 2 with the second insulating layers 8 disposed therebetween as shown in FIG. 2F.

Figure 2G:
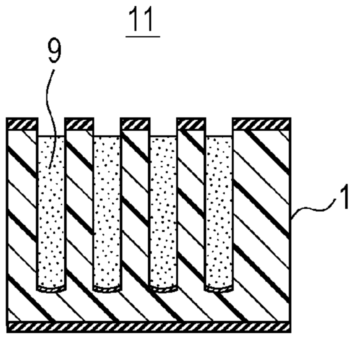

In this example, metal filled into the recessed sections 3 was gold. A gold plating solution used was MICROFAB Au 1101 available from Electroplating Engineers of Japan Ltd. Plating was performed at a plating solution temperature of 60° C. and a current density of 0.1 A/$dm^2$ for ten hours by applying electric power to the seed layers 10, whereby gold plating layers 9 with a thickness of 50 μm were formed. The silicon substrate 1 was taken out of the gold plating solution, was washed with pure water, and was then dried by nitrogen blowing, whereby a structure 11 including the gold plating layers 9 was obtained as shown in FIG. 2G. The gold plating layers 9 were arranged in the silicon substrate 1, were mesh-structured, and had a high aspect ratio, that is, a height of 50 μm and a width of 2 μm.

The structure 11 was observed from the top portions 4 with an X-ray microscope. Silicon portions transmitted X-rays and portions of the gold plating layers 9 absorbed X-rays; hence, high contrast was obtained.

Comparative Example 1

In this comparative example, substantially the same silicon structure as that described in Example 1 was used as a silicon substrate except that the silicon structure included no first insulating layer disposed on top portions of protruding sections. The silicon structure included 2 μm ϕ silicon grids, arranged at a pitch of 4 μm, having a height of about 65 μm. Second insulating layers made of a monomethylpolysiloxane were formed in substantially the same manner as that described in Example 1. Chromium sub-layers and gold sub-layers for forming seed layers were formed in that order using an electron beam evaporation system so as to have a thickness of about 7.5 nm and a thickness of about 50 nm, respectively. This allowed the seed layers to be formed above bottom portions of recessed sections arranged in a silicon section with the second insulating layers disposed therebetween.

A gold plating solution used was MICROFAB Au 1101 available from Electroplating Engineers of Japan Ltd. Plating was performed at a plating solution temperature of 60° C. and a current density of 0.1 A/$dm^2$ by applying electric power to the seed layers. After a lapse of two hours, it was observed that plating layers were precipitated on the top portions of the protruding sections. After a lapse of two hours, plating was stopped and the protruding sections were observed in cross section. It was observed that the plating layers on the top portions of the protruding sections blocked upper portions of recessed sections to form voids.

Comparative Example 2

In this comparative example, gold plating was performed in substantially the same manner as that described in Example 1 except that no second insulating layers made of a monomethylpolysiloxane were formed sidewalls or bottom portions of recessed sections. After a lapse of four hours from the start of plating, plating was stopped and the protruding sections were observed in cross section. It was observed that plating layers were precipitated on the sidewalls of the protruding sections to form voids.

Example 2

FIGS. 3A to 3E are illustrations showing steps of a method of manufacturing a structure according to Example 2 of the present invention. Second insulating layers used in this example were made of a dimethylpolysiloxane. In this example, the following wafer was used: a silicon wafer, equipped with two mirror-like surfaces, having a diameter of 100 mm (four inches) and a thickness of 525 μm. A Cr layer with a thickness of 200 nm was formed on the silicon wafer by an electron beam evaporation process. A positive resist was applied onto the Cr layer and was patterned by semiconductor photolithography, whereby a resist pattern having 2 μm ϕ sub-patterns two-dimensionally arranged at a pitch of 4 μm was formed. Exposed portions of the Cr layer were etched off using an aqueous Cr-etching solution, whereby the silicon wafer was partly exposed.

Figure 3A:
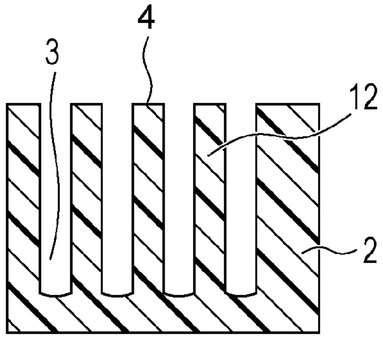
FIGS. 3A to 3E are illustrations showing a step of a method of manufacturing a structure according to Example 2 of the present invention.

RIE was performed by a Bosch process in such a manner that the Cr layer was used as a mask and etching and the deposition of a sidewall-protecting layer were alternately performed using a $SF_6$ gas and a $C_4F_8$ gas, respectively. As a result of RIE, recessed sections 3 with a depth of 65 μm and protruding sections 12 were formed. The positive resist and the Cr layer were removed by oxygen plasma ashing. This allowed a silicon structure including 2 μm ϕ silicon grids, arranged at a pitch of 4 μm, having a height of about 65 μm to be obtained as shown in FIG. 3A.

Figure 3D:
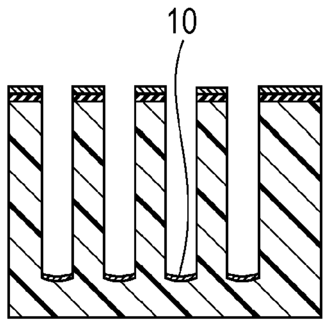
Figure 3B:
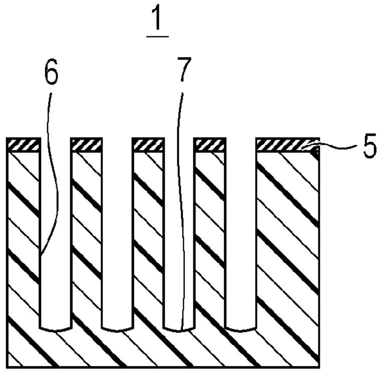

$SiO_2$ was deposited on top portions 4 of the protruding sections 12 by vacuum sputtering, whereby a first insulating layer 5 with a thickness of 100 nm was formed thereon. In this example, the silicon structure was used as a silicon substrate 1. The silicon substrate 1 included the first insulating layer 5 disposed on the top portions 4 of the protruding sections 12 formed by etching a silicon section 2 as shown in FIG. 3B.

Figure 3E:
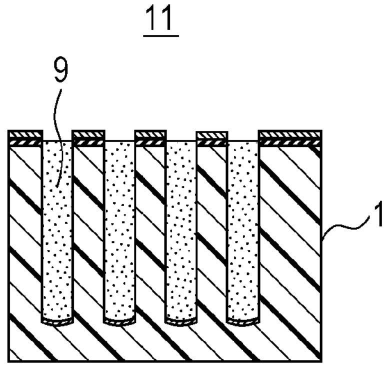
Figure 3C:
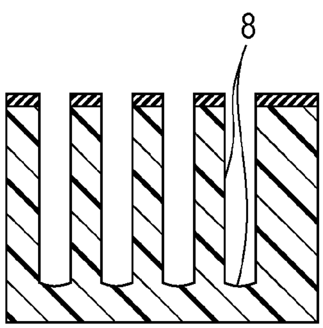

A petri dish containing dimethoxydimethylsilane, a petri dish containing pure water, and the silicon substrate 1 were placed on a 90° C. hotplate and were covered with a petri dish lid. This allowed dimethoxydimethylsilane to be vaporized. The vapor of dimethoxydimethylsilane entered the recessed sections 3, resulting in the formation of second insulating layers 8 made of a dimethylpolysiloxane as shown in FIG. 3C. Since the silicon substrate 1 was heated on the hotplate, the dimethoxydimethylsilane vapor was not condensed on the silicon substrate 1. After a lapse of four hours, the silicon substrate 1 was transferred onto a 150° C. hotplate and was then heated for 30 minutes.

Chromium sub-layers and gold sub-layers for forming seed layers 10 were formed in that order using an electron beam evaporation system so as to have a thickness of about 7.5 nm and a thickness of about 50 nm, respectively. This allowed the seed layers 10 to be formed above bottom portions 7 of the recessed sections 3 with the second insulating layers 8 disposed therebetween as shown in FIG. 3D.

In this example, metal filled into the recessed sections 3 was gold. A gold plating solution used was MICROFAB Au 1101 available from Electroplating Engineers of Japan Ltd. Plating was performed at a plating solution temperature of 60° C. and a current density of 0.1 A/$dm^2$ for ten hours by applying electric power to the seed layers 10, whereby gold plating layers 9 with a thickness of 50 μm were formed. The silicon substrate 1 was taken out of the gold plating solution, was washed with pure water, and was then dried by nitrogen blowing, whereby a structure 11 including the gold plating layers 9 was obtained as shown in FIG. 3E. The gold plating layers 9 were arranged in the silicon substrate 1, were mesh-structured, and had a high aspect ratio, that is, a height of 50 μm and a width of 2 μm.

The structure 11 was observed from the top portions 4 with an X-ray microscope. Silicon portions transmitted X-rays and portions of the gold plating layers 9 absorbed X-rays; hence, high contrast was obtained.

Example 3

In this example, a structure was manufactured by the method shown in FIG. 1. A photoresist was used to form a first insulating layer 5. Furthermore, the following wafer was used: a silicon wafer, equipped with two mirror-like surfaces, having a diameter of 100 mm (four inches) and a thickness of 525 μm. The following pattern was formed on the silicon wafer by semiconductor photolithography using the photoresist for forming the first insulating layer 5: a 7 μm high resist pattern having 2 μm ϕ sub-patterns two-dimensionally arranged at a pitch of 4 μm.

RIE was performed by a Bosch process in such a manner that the resist pattern was used as a mask and etching and the deposition of a sidewall-protecting layer were alternately performed using a $SF_6$ gas and a $C_4F_8$ gas, respectively. As a result of RIE, recessed sections 3 with a depth of 65 μm and protruding sections 12 were formed. This allowed a silicon structure including 2 μm ϕ silicon grids, arranged at a pitch of 4 μm, having a height of about 65 μm to be obtained. A piece of the photoresist remained on top portions 4 of the protruding sections 12. In this example, the photoresist piece was used as the first insulating layer 5. The silicon structure was used as a silicon substrate 1. The silicon substrate 1 included the first insulating layer 5 disposed on the top portions 4 of the protruding sections 12 formed by etching a silicon section 2.

A petri dish containing dimethoxydimethylsilane, a petri dish containing pure water, and the silicon substrate 1 were placed on a 90° C. hotplate and were covered with a petri dish lid. This allowed dimethoxydimethylsilane to be vaporized. The vapor of dimethoxydimethylsilane entered the recessed sections 3, resulting in the formation of second insulating layers 8 made of a dimethylpolysiloxane. Since the silicon substrate 1 was heated on the hotplate, the dimethoxydimethylsilane vapor was not condensed on the silicon substrate 1. After a lapse of four hours, the silicon substrate 1 was transferred onto a 150° C. hotplate and was then heated for 30 minutes.

Chromium sub-layers and gold sub-layers for forming seed layers 10 were formed in that order using an electron beam evaporation system so as to have a thickness of about 7.5 nm and a thickness of about 50 nm, respectively. This allowed the seed layers 10 to be formed above bottom portions 7 of the recessed sections 3 with the second insulating layers 8 disposed therebetween.

In this example, metal filled into the recessed sections 3 was gold. A gold plating solution used was MICROFAB Au 1101 available from Electroplating Engineers of Japan Ltd. Plating was performed at a plating solution temperature of 60° C. and a current density of 0.1 $A/dm^2$ for ten hours by applying electric power to the seed layers 10, whereby gold plating layers 9 with a thickness of 50 μm were formed. The silicon substrate 1 was taken out of the gold plating solution, was washed with pure water, and was then dried by nitrogen blowing, whereby a structure 11 including the gold plating layers 9 was obtained. The gold plating layers 9 were arranged in the silicon substrate 1, were mesh-structured, and had a high aspect ratio, that is, a height of 50 μm and a width of 2 μm.

The structure 11 was observed from the top portions 4 with an X-ray microscope. Silicon portions transmitted X-rays and portions of the gold plating layers 9 absorbed X-rays; hence, high contrast was obtained.

Example 4

Figure 4:
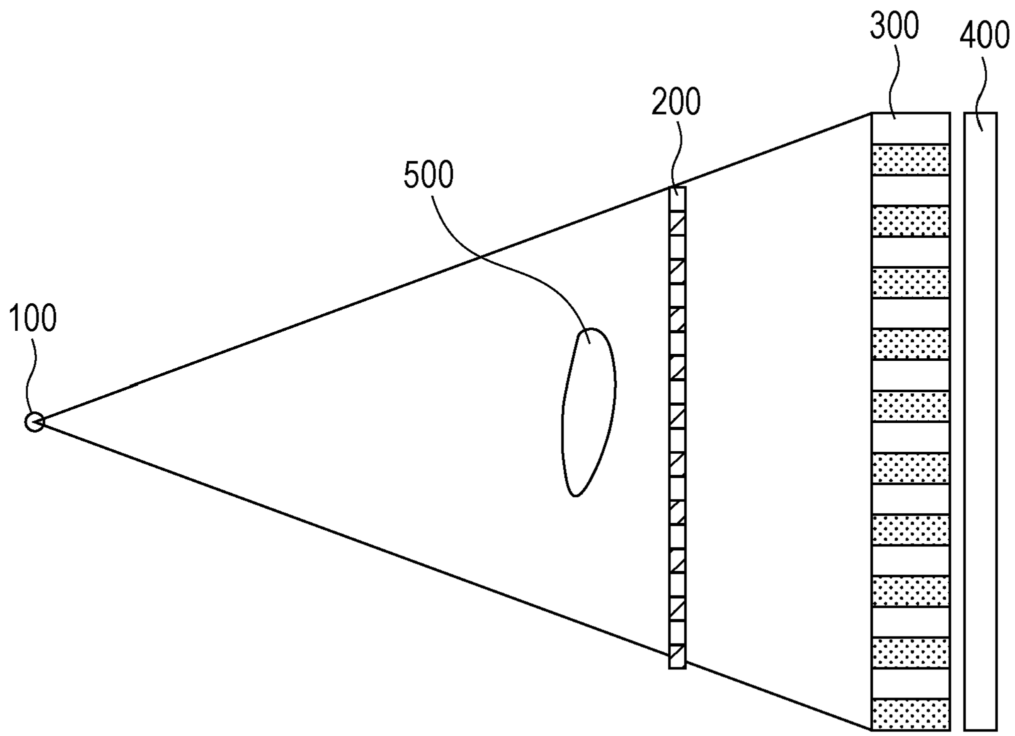
FIG. 4 is a configuration diagram of an imaging apparatus according to an embodiment of the present invention.

In this example, an imaging apparatus performing a Talbot interference method is described with reference to FIG. 4. In the imaging apparatus, the structure described in any one of the above embodiments and examples is used as an X-ray shield grating.

The imaging apparatus includes an X-ray source 100 emitting a spatially coherent X-ray, a diffraction grating 200 for periodically modulating the phase of the X-ray, a shield grating 300 including X-ray shielding sections and X-ray permeable sections, and a detector 400 detecting the X-ray. The shield grating 300 includes the structure described in any one of the above embodiments and examples.

The sample 500 is placed between the X-ray source 100 and the diffraction grating 200, information about the phase shift of the X-ray due to the sample 500 is detected by the detector 400 in the form of moire. That is, the imaging apparatus takes an image of the sample 500 by detecting moire having the phase information of the sample 500. On the basis of this detection result, phase retrieval is performed by Fourier transform or the like, whereby a phase image of the sample 500 can be obtained.

Preferred embodiments of the present invention have been described above. The present invention is not limited to these embodiments. Various modifications and variations can be made within the scope of the present invention. Technical elements described herein or with reference to the attached drawings exhibit technical utility alone or in combination and are not limited to combinations described in the claims as filed. Techniques described herein or with reference to the attached drawings simultaneously achieve a plurality of purposes and have technical utility by achieving one of the purposes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-030010 filed Feb. 15, 2011, which is hereby incorporated by reference herein in its entirety.

What is claimed is:

1. A method of manufacturing a structure, comprising:

a step of preparing a substrate including a silicon section, recessed sections formed by etching the silicon section, protruding sections formed by etching the silicon section, and a first insulating layer disposed on top portions of the protruding sections;

a step of forming second insulating layers on sidewalls and bottom portions of the recessed sections;

a step of forming seed layers containing metal above the bottom portions of the recessed sections having the second insulating layers thereon; and a step of forming plating layers in such a manner that the recessed sections having the seed layers are filled with metal by electroplating, wherein the second insulating layers contain an organopolysiloxane having at least one of a partial structure represented by the following formula (1) and a partial structure represented by the following formula (2):

(1)

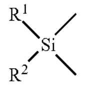

-continued (2)

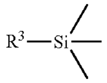

where $R^1$, $R^2$, and $R^3$ represent alkyl groups identical to or different from each other.

2. The method according to claim 1, wherein the second insulating layers are formed in such a manner that a precursor of the organopolysiloxane is vaporized and is then subjected to hydrolysis and polycondensation in a vapor state.

3. The method according to claim 2, wherein the organopolysiloxane precursor is a silane coupling agent.

4. The method according to claim 1, wherein the first insulating layer is made of $SiO_2$.

5. The method according to claim 1, wherein the metal is gold or a gold alloy.

6. The method according to claim 1, wherein the recessed sections have an aspect ratio (height h/width w) of 5 or more.

7. A structure comprising:

a silicon substrate including recessed sections and protruding sections;

a first insulating layer disposed on top portions of the protruding sections;

second insulating layers formed on sidewalls and bottom portions of the recessed sections; and metal filled in the recessed sections having the second insulating layers, wherein the second insulating layers contain an organopolysiloxane having at least one of a partial structure represented by the following formula (1) and a partial structure represented by the following formula (2):

(1)

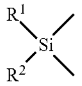

(2)

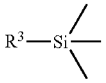

where $R^1$, $R^2$, and $R^3$ represent alkyl groups identical to or different from each other.

8. An imaging apparatus for taking an image of a sample, comprising:

a diffraction grating diffracting an X-ray emitted from an X-ray source;

a shield grating shielding a part of the X-ray diffracted by the diffraction grating; and a detector detecting the X-ray passing through the shield grating, wherein the shield grating includes the structure according to claim 7.

* * * * *